US006432055B1

(12) United States Patent
Carp et al.

(10) Patent No.: US 6,432,055 B1
(45) Date of Patent: Aug. 13, 2002

(54) MEDICAL ULTRASONIC IMAGING SYSTEM WITH THREE-STATE ULTRASONIC PULSE AND IMPROVED PULSE GENERATOR

(75) Inventors: Stuart L. Carp, Menlo Park; Lazar Shifrin, San Jose; Samuel H. Maslak, Woodside, all of CA (US)

(73) Assignee: Acuson Corporation, Mountain View, CA (US)

( * ) Notice: Subject to any disclaimer, the term of this patent is extended or adjusted under 35 U.S.C. 154(b) by 97 days.

(21) Appl. No.: 09/607,806

(22) Filed: Jun. 30, 2000

(51) Int. Cl.[7] .............................................. A61B 8/00
(52) U.S. Cl. ..................................................... 600/437
(58) Field of Search ............................... 600/437, 442, 600/443, 447, 448; 604/22; 73/602, 603, 614, 625, 626; 367/7, 11, 130, 138, 153, 2; 310/317, 316.01

(56) References Cited

U.S. PATENT DOCUMENTS

| | | | |
|---|---|---|---|
| 4,109,644 A | * | 8/1978 | Kojima ........................... 367/2 |
| 4,449,068 A | * | 5/1984 | Johnson et al. ......... 310/316.01 |
| 5,425,704 A | * | 6/1995 | Sakurai et al. ................. 604/22 |
| 5,675,554 A | | 10/1997 | Cole et al. |
| 5,825,117 A | * | 10/1998 | Ossmann et al. ........... 310/317 |
| 5,833,614 A | | 11/1998 | Dodd et al. |
| 6,050,945 A | * | 4/2000 | Peterson et al. ............. 600/443 |
| 6,074,346 A | * | 6/2000 | Oppelt ......................... 600/437 |

OTHER PUBLICATIONS

Fig. A1–A15 illustrating transmit waveforms (Dec., 1998).
Fig. B1–B3 illustrating transmit waveforms (Nov., 1998).
Fig. C1–C7 illustrating transmit waveforms (Nov., 1998).
The Quest for Magic Sinewaves (Upping Power Electronics Efficiency) Coptright by Don Lancaster (1997) pp. 1–7.

* cited by examiner

Primary Examiner—Francis J. Jaworski
Assistant Examiner—Ali M. Imam

(57) ABSTRACT

A three-state, pulse width modulated, bipolar waveform is constructed by summing a first component with an inverted, time-shifted version of the first component. By properly selecting the time interval for the time shift of the second component, frequency filtering benefits can be obtained. The three-state waveform is generated by a switched voltage source that provides a low, constant source impedance for all three voltage states.

57 Claims, 13 Drawing Sheets

ω(t)

w(t)    PULSE SPECTRUM

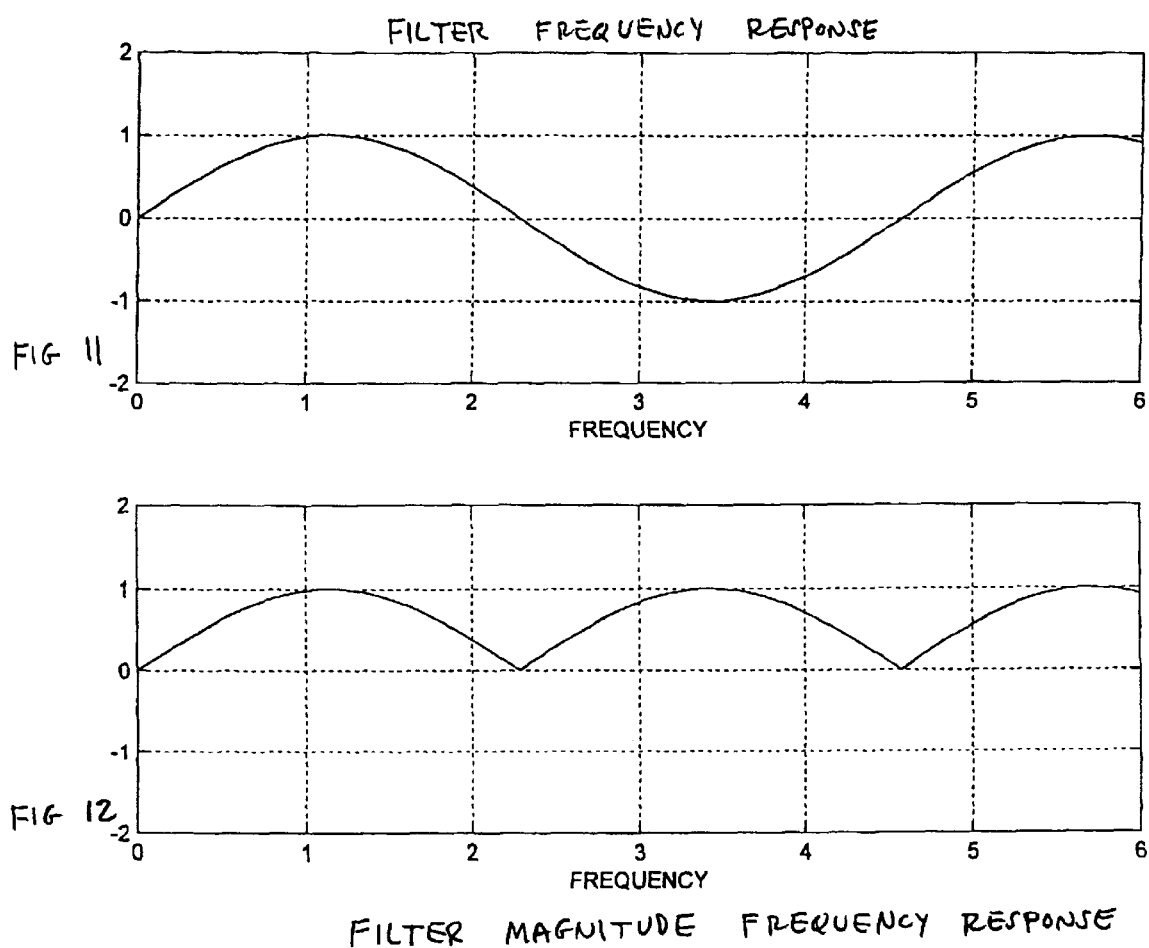

FILTERED PULSE SPECTRUM

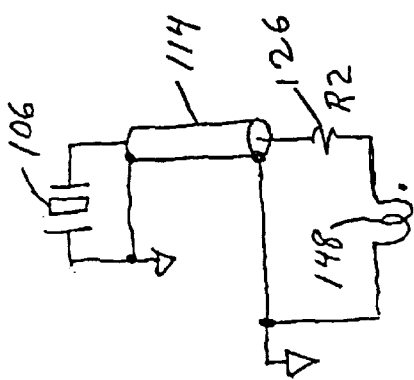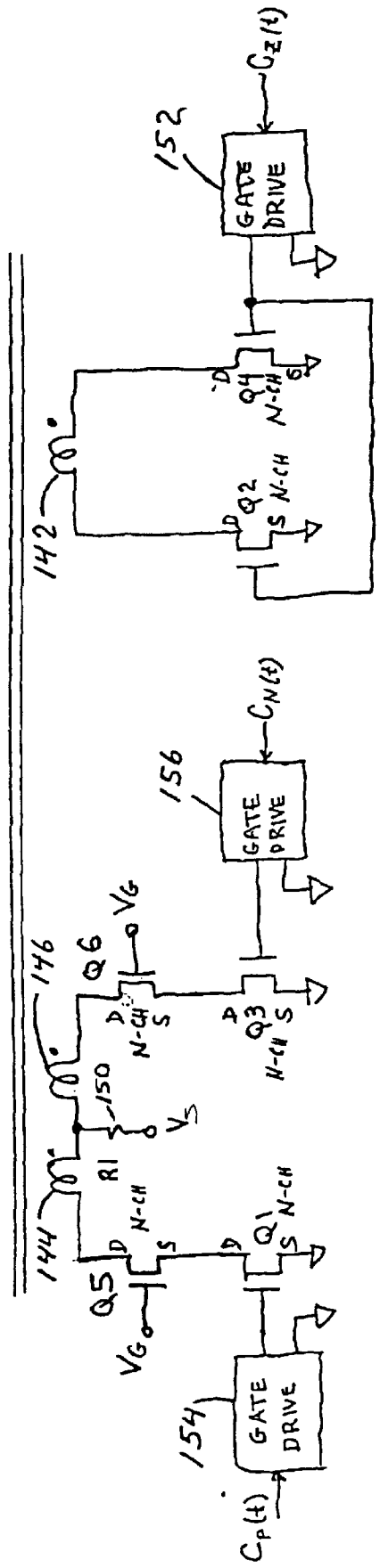
FIG 22

US 6,432,055 B1

MEDICAL ULTRASONIC IMAGING SYSTEM WITH THREE-STATE ULTRASONIC PULSE AND IMPROVED PULSE GENERATOR

BACKGROUND

The present invention relates to medical ultrasonic imaging systems, and in particular to improved ultrasonic transmit pulses and transmit pulse generators for such systems.

Fundamental, harmonic, and subharmonic mode ultrasound imaging are all improved by controlling the bandwidth of the frequency spectrum of the transmitted ultrasonic pulse. This bandwidth is preferably limited to frequencies around the fundamental, and is preferably sharply reduced at specified harmonics and subharmonics of the fundamental.

One prior-art approach is to select the number of cycles of a carrier frequency that are transmitted in a square wave pulse burst. A greater number of carrier cycles in the burst corresponds to a narrower signal bandwidth. Another approach is to use a bipolar uniform square wave pulse train, which has less energy around the second harmonic frequency than does a unipolar uniform square wave pulse train of the same length.

Another approach is to use a carrier wave that is modulated by a gradually rising and gradually falling amplitude envelope. This approach requires an analog transmitter capable of generating output voltages at a large number of different levels. Cole U.S. Pat. No. 5,675,554, assigned to the assignee of the present invention, provides one example of this approach.

Dodd U.S. Pat. No. 5,833,614, also assigned to the assignee of the present invention, discusses several types of pulse width modulated ("PWM") signals that can be used to approximate a carrier wave modulated by a gradually rising and gradually falling amplitude envelope. FIG. 3 of the Dodd patent shows a unipolar PWM signal having two amplitude levels. FIGS. 5 and 6 show bipolar PWM signals having three voltage levels (+V, 0V, -V). Note that the 0V level is held for some length of time within the duration of the pulse burst, greater than an instantaneous time.

There are a number of prior-art approaches to hardware for generating three level ultrasonic pulses. FIG. 1 shows one prior-art switched voltage supply that uses both a positive voltage power supply and a negative voltage power supply. Two FETs are used as switches to drive the load alternately with a positive-going and a negative-going waveform. When either FET is switched on, the output impedance is low, on the order of a few ohms. Normally, the waveforms generated by these types of transmitters are characterized by a 50% duty cycle and are held in the zero value state only before and after transmitting the pulse burst, not during the pulse burst. Both FETs are switched off in the zero value state, and in this state the output impedance of the FETs is high, approximately equal to the capacitive reactance of the two FETs. As shown in FIG. 1, a resistor is connected between the junction of the FETs and ground to lower the impedance in the zero value state. This shunt resistor brings the disadvantage that substantial power is wasted in the resistor when the transmitter is in the positive or negative output states. The transmitter of FIG. 1 also has the disadvantage that it requires both positive and negative high voltage power supplies. Furthermore, the gate drivers for all of the FETs are referenced to a voltage other than ground, which increases their circuitry complexity and cost. Low second-harmonic distortion performance requires that the generated waveform have excellent symmetry. This is difficult to achieve with the transmitter of FIG. 1.

FIG. 2 shows another prior-art transmitter that uses a transformer and N-channel FETs to form a bipolar, push-pull transmitter. In the transmitter of FIG. 2, the FETs are all operated as switches. The transmitter of FIG. 2 is capable of excellent waveform symmetry, and it uses ground referenced gate drivers for all of the FETs. Furthermore, the output impedance of the transmitter is low in either the positive voltage state or the negative voltage state. However, the output impedance increases to the value of R in the zero voltage state when both FETs are in the open-circuit state. If both FETs were placed in the closed-circuit state, the output voltage would be zero and the output impedance seen looking back into the transformer would be low, but the circuit would draw excessive current from the power supply as the current through the two halves of the center-tapped transformer primary would develop magnetic fluxes that cancel each other.

The prior-art transmitter of FIG. 3 is similar to that of FIG. 2, but in this case the FETs are operated as current sources, not as switches. The drives to the FETs are controlled to keep them operating in the pentode region of their drain family characteristic, where they have a high output impedance and can be considered as current sources. In this case, the output impedance of the circuit is set by the resistor R (neglecting the output capacitance of the FETs and the parasitic reactances of the transformers). The FETs can be driven at their gates or their sources. The circuit of FIG. 3 is power inefficient. When the output is in the positive or negative voltage state, the transmitter delivers wasted current to the resistor R. Power is also wasted in the FETs when they are operated as current sources, since it is necessary to maintain a drain-to-source voltage across them to keep them in the pentode region. Power is dissipated across the FETs because they have a current flowing through them at the same time that there is a voltage across them.

Thus, a need presently exists both for improved three-state transmit pulses that suppress energy at selected harmonic frequencies, and for improved transmit generators that are capable of generating three-state pulses efficiently, symmetrically and economically.

SUMMARY

By way of introduction, the preferred embodiments described below use a new type of three-state, PWM transmit waveform that is the sum of two components. The first component is a two-state waveform at 0V and +V, and it has the desired fundamental frequency characteristics. The second component is a time-shifted, inverted version of the first component at voltages 0V and -V. By properly selecting the amount by which the second component is time-shifted relative to the first component, transmitted power at any selected harmonic frequency can be further reduced.

This improved three-state PWM waveform is preferably generated with a switched voltage source that provides low, substantially identical source impedances in each of the three states (+V, 0V, -V). Because the source impedance is low in all three states, the transmitter operates efficiently. Because the source impedance is constant in all three states, the transmitter is able to generate a symmetrical transmit waveform with excellent suppression of second harmonic components. One preferred embodiment described below achieves these important advantages using only N-channel switches controlled by gate drivers that are all referenced to ground. This embodiment has particularly low fabrication cost.

The switched voltage sources described below can be used to generate other waveforms, including waveforms described in the above-referenced Dodd patent. Additionally, these voltage sources can be adapted to generate waveforms with more than three voltage levels. The low source impedance of these switched voltage sources allows accurate generation of waveforms having two or more pulses of the same voltage polarity that are separated by a short-duration zero volt interval.

The foregoing paragraphs have been intended by way of introduction, and they are not intended to limit the scope of the following claims.

BRIEF DESCRIPTION OF THE DRAWINGS

FIGS. 10, 11, 12 and 13 are waveform diagrams used to explain the operation of the block diagram of FIG. 9.

FIGS. 20, 21, and 22 are block diagrams of alternative embodiments of the switched voltage source of FIG. 15.

DETAILED DESCRIPTION OF THE PRESENTLY PREFERRED EMBODIMENTS

The following sections will first discuss an improved, pulse width modulated, three-state ultrasonic transmit pulse and then a number of transmitters for generating such pulses.

The Transmit Pulse

Figure 1:
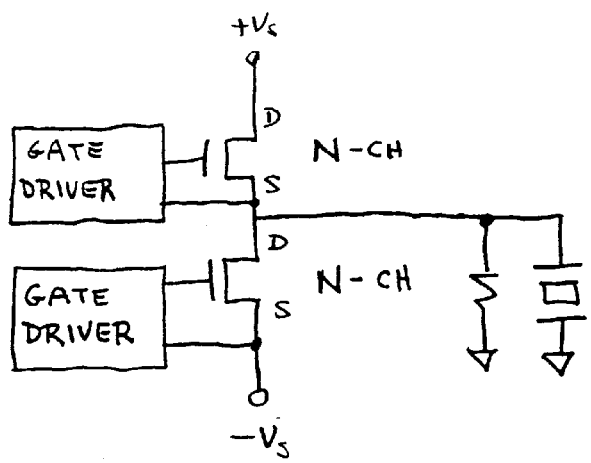
FIGS. 1, 2 and 3 are block diagrams of three prior-art ultrasonic waveform generators.
Figure 2:
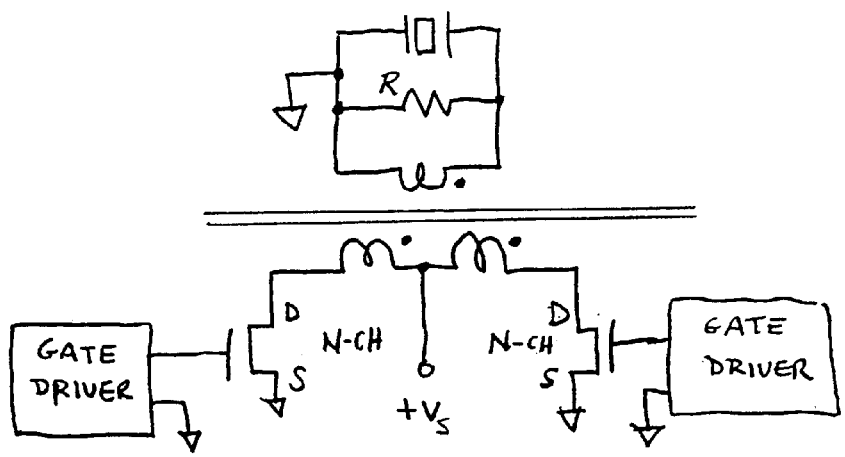
Figure 3:
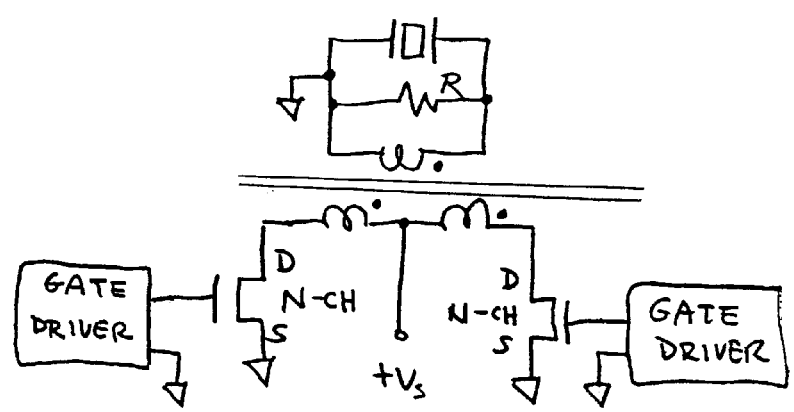
Figure 4:
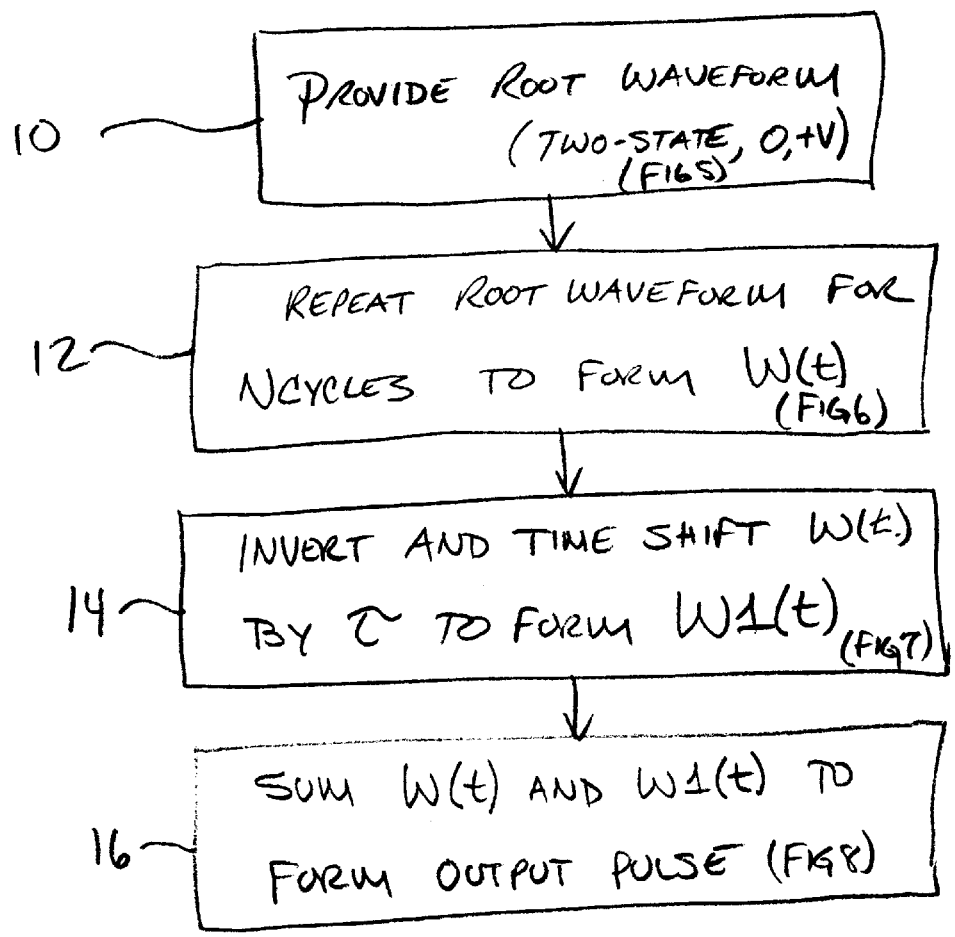
FIG. 4 is a block diagram of a method for creating a three-state, pulse width modulated ultrasonic transmit waveform.
Figure 5:
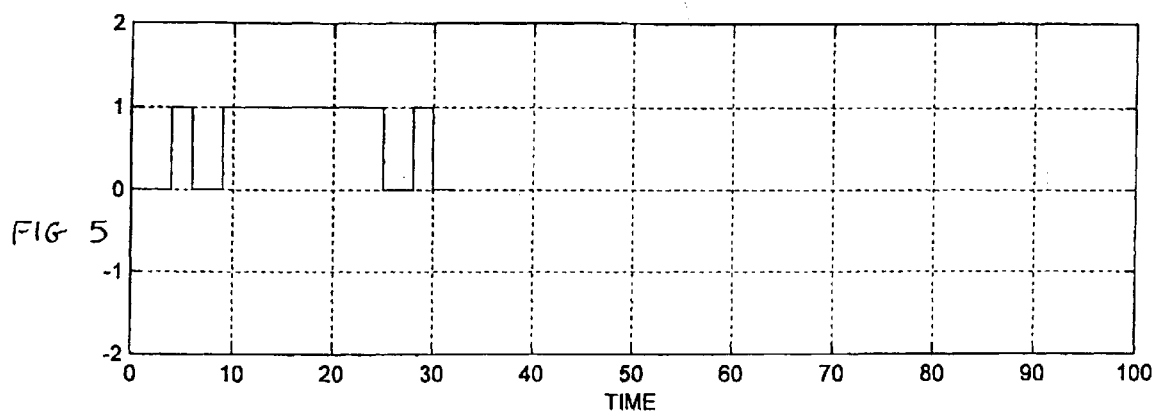
FIGS. 5–8 are waveform diagrams of waveforms referenced in FIG. 4.

FIG. 4 is a block diagram of a method for generating an improved three-state ultrasonic transmit pulse. As shown at 10, first a unipolar, two-state root waveform is provided having the desired frequency content and/or temporal characteristics. FIG. 5 shows one example of such a root waveform. In FIGS. 5–8, time is plotted on the X axis and voltage on the Y axis. Time is measured in units of fractions of the period of the fundamental frequency of the root waveform. In alternative embodiments, the root waveform may be specified in either the time domain or the frequency domain.

Figure 6:
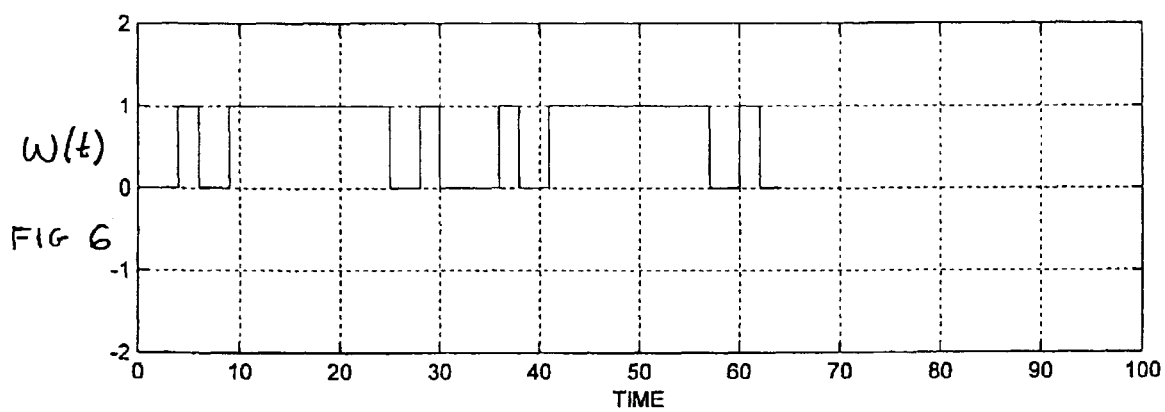

Next, in block 12, the root waveform is repeated for multiple cycles based on the desired pulse frequency content or the desired time duration of the transmit pulse. FIG. 6 shows one example, in which the root waveform of FIG. 5 has been repeated for a total of two cycles to form the waveform W(t). The time delay between the multiple cycles of the repeated root waveform can be adjusted to give additional control over the frequency spectrum of the ultrasonic transmit pulse. For example, the time delay can be adjusted to provide increased suppression at particular frequencies around a harmonic of the transmit spectrum. This degree of adjustment is particularly advantageous in Tissue Harmonic Imaging modes. The time delay can also be adjusted to optimize the trade off between the frequency domain and the time domain characteristics of the waveform. This can be done to obtain a favorable frequency spectrum while at the same time avoiding narrow width pulse shapes that would require impractically fast switching circuits in the transmitter hardware. Note that the waveform W(t) is a square wave that alternates between the voltage levels 0V and +V. In FIG. 6 a binary notation is shown in which 0 is used for each clock cycle in which W(t) is equal to 0V, and 1 is used for each clock cycle in which W(t) is equal to +V. In this example there are 32 clock cycles in each fundamental period.

Figure 7:
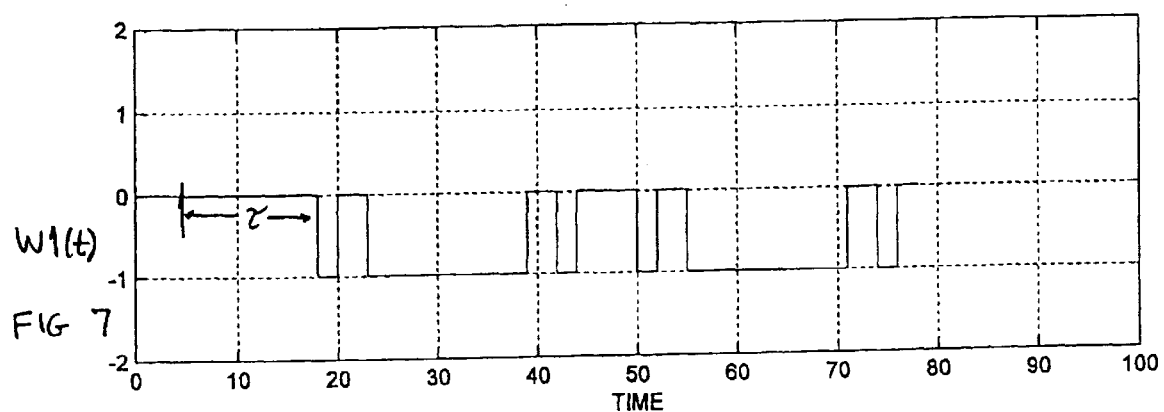

In block 14 the waveform W(t) is inverted and time shifted by a time interval $\tau$ to form the waveform W1(t) graphed in FIG. 7. In the example of FIG. 7, $\tau$ equals 14/32 of the fundamental period.

Figure 8:
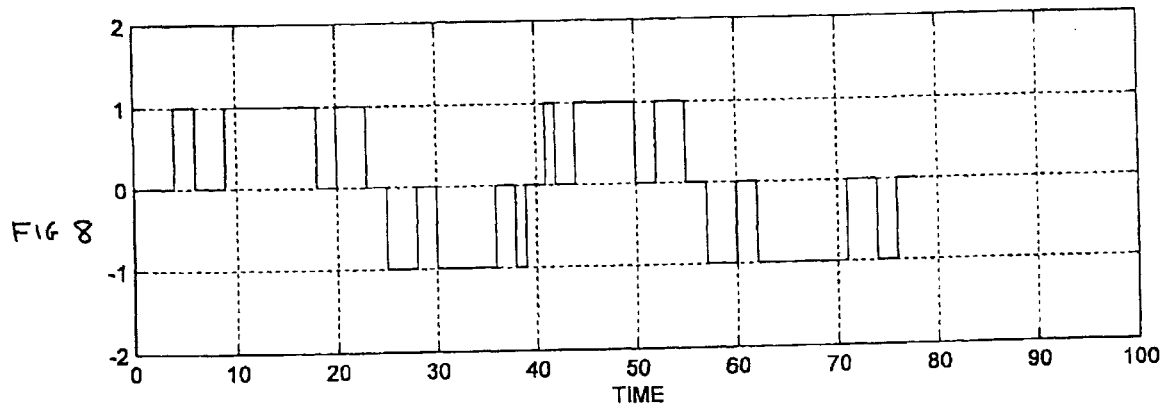

In block 16 W(t) and W1(t) are summed to form the desired ultrasonic pulse (FIG. 8). Note that the waveform of FIG. 8 is in the 0V state whenever W(t) and W1(t) are both equal to 0 or both equal to their respective non-zero levels. The ultrasonic waveform of FIG. 8 has been designed to suppress transmitted energy at the second harmonic of the fundamental frequency. Note that the waveform of FIG. 8 is a bi-polar, square wave signal having three voltage levels (+V, 0V, –V), and that the pulse of FIG. 8 is a pulse width modulated signal.

Note that the 0V level is held in the pulse of FIG. 8 for an extended time period that is more than an instant, as when a continuously varying sinusoidal voltage passes through 0V. In general, the waveform of FIG. 8 will be characterized by a center frequency $f_0$ (the fundamental frequency) and an associated center period $\tau_0$ ($\tau_0=1/f_0$). The 0V state is held at least once during the pulse of FIG. 8 for a time period no less than $(N*\tau_0)/128$, where N is preferably $\geq 1$, more preferably $\geq 2$, and on occasion $\geq 4$ or even $\geq 8$.

Figure 9:
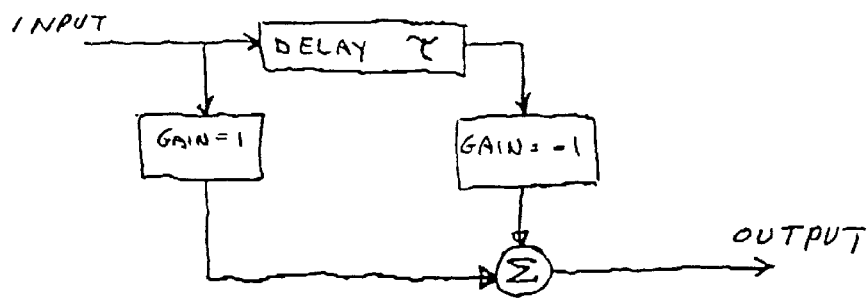
FIG. 9 is a block diagram of a model of the method of FIG. 4.

FIG. 9 is a block diagram that represents a model of blocks 14 and 16 of FIG. 4. As shown in FIG. 9, the input signal is summed with a time delayed, inverted version of the input signal to produce the output signal. The model of FIG. 9 is a representation of a conventional two-tap FIR filter. Thus, the output signal generated by block 16 of FIG. 4 is the same as if we had taken the waveform W(t) of block 12 of FIG. 4 and filtered it with an FIR filter. The method of FIG. 4 therefore provides all of the benefits of spectral filtering without requiring the hardware or software of an FIR filter. This is because the filter characteristics are built into the waveform itself.

Figure 10:
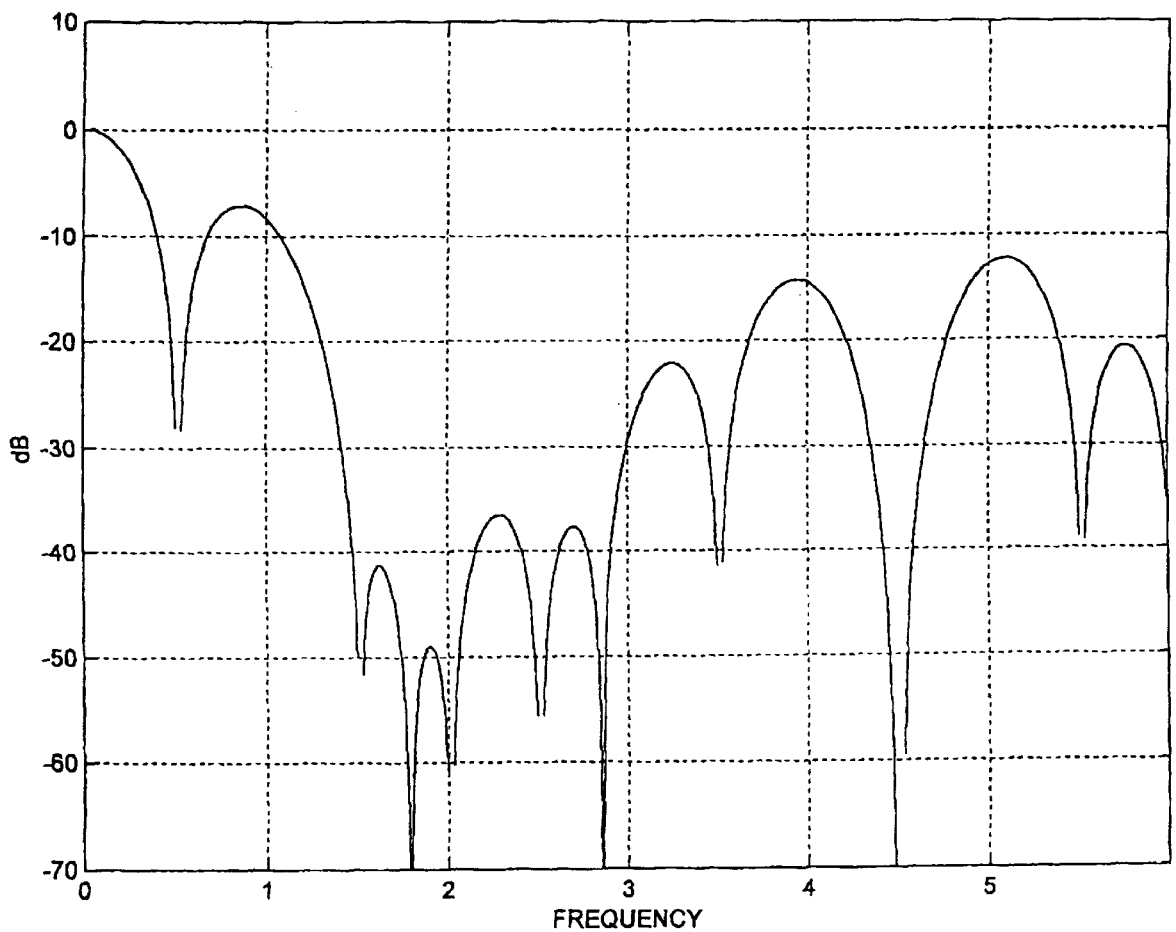
Figure 13:
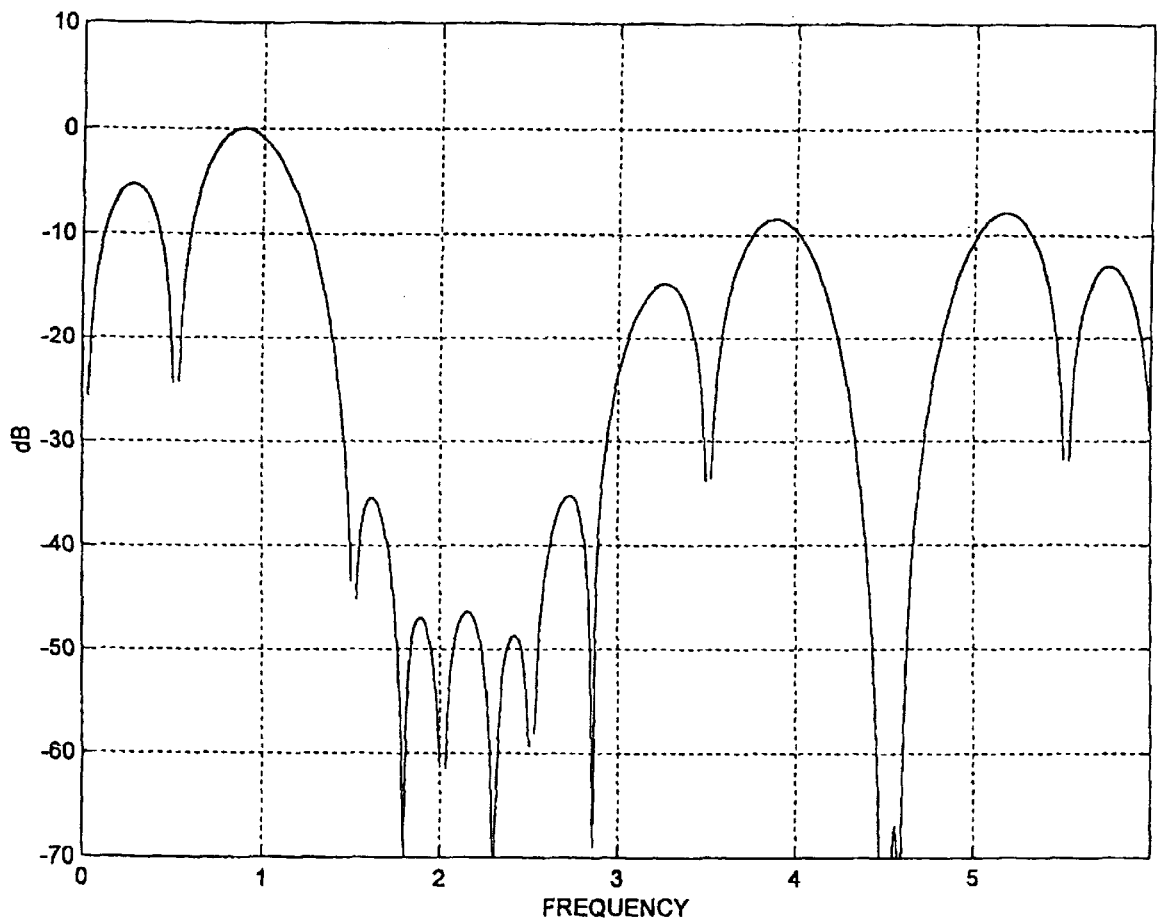

The waveform W(t) has an associated frequency spectrum as shown in FIG. 10. In this example, the goal was to retain energy at the frequency $f_0$ but to reduce energy at frequencies around $2f_0$. In FIGS. 10–13, the X-axis is plotted in multiples of $f_0$. The effect of blocks 14 and 16 of FIG. 4 is to apply a filter to the waveform W(t) having a filter frequency response as shown in FIG. 11. A filter with the frequency response of FIG. 11 passes energy at the frequency $f_0$ and attenuates frequencies around $2f_0$. When only the magnitude of the frequency response is considered, the filter frequency response is shown in FIG. 12. When the pulse spectrum of FIG. 10 is passed through the filter frequency response of FIG. 12, the output is the sum of the frequency responses graphed in FIGS. 10 and 12 (after converting the frequency response of FIG. 12 to logarithmic units), as shown in FIG. 13. The output of the filter has reduced energy at the second harmonic (around $2f_0$) relative to the fundamental (at $f_0$).

The filter operation of blocks 14 and 16 of FIG. 4 can be described as the function $\sin(\pi f \tau)$, where output frequency spectrum=input frequency spectrum·$\sin(\pi f \tau)$.

In this example, we want a zero in the filter response at $f=2f_0$ and therefore $\sin(\pi 2f_0\tau)$ is set equal to zero. This is the case when $2f_0\tau=1$, or $\tau=\frac{1}{2}f_0$. Therefore the desired filter function is sin $$\sin\left(\frac{\pi f}{2f_0}\right)$$

in the frequency domain. In the time domain this corresponds to summing a pulse with a time-shifted, inverted version of that pulse.

The advantage of this approach is that the harmonic suppression benefits of a filter are obtained without the need for any additional hardware or software. The frequencies of the nulls in the filter function $\sin(\pi f \tau)$ are determined by $\tau$, the time delay. We can change the frequency of the null by using a different value of $\tau$ in creating the self-filtering waveform. For example, l can be made to vary from $\frac{1}{2}f_0$. A typical variation in u might be in increments of $f_0/16$ or $f_0/32$, where $1/f_0$ is the period of the fundamental transmit frequency. Of course, the present invention is not limited to the specific examples discussed above. A wide variety of root waveforms can be used, depending upon the desired spectral characteristics of the final waveform. Similarly, the number of cycles of the root waveform used to form W(t) can be varied, as can the offset time interval $\tau$.

The Transmit Pulse Generator

Figure 14:
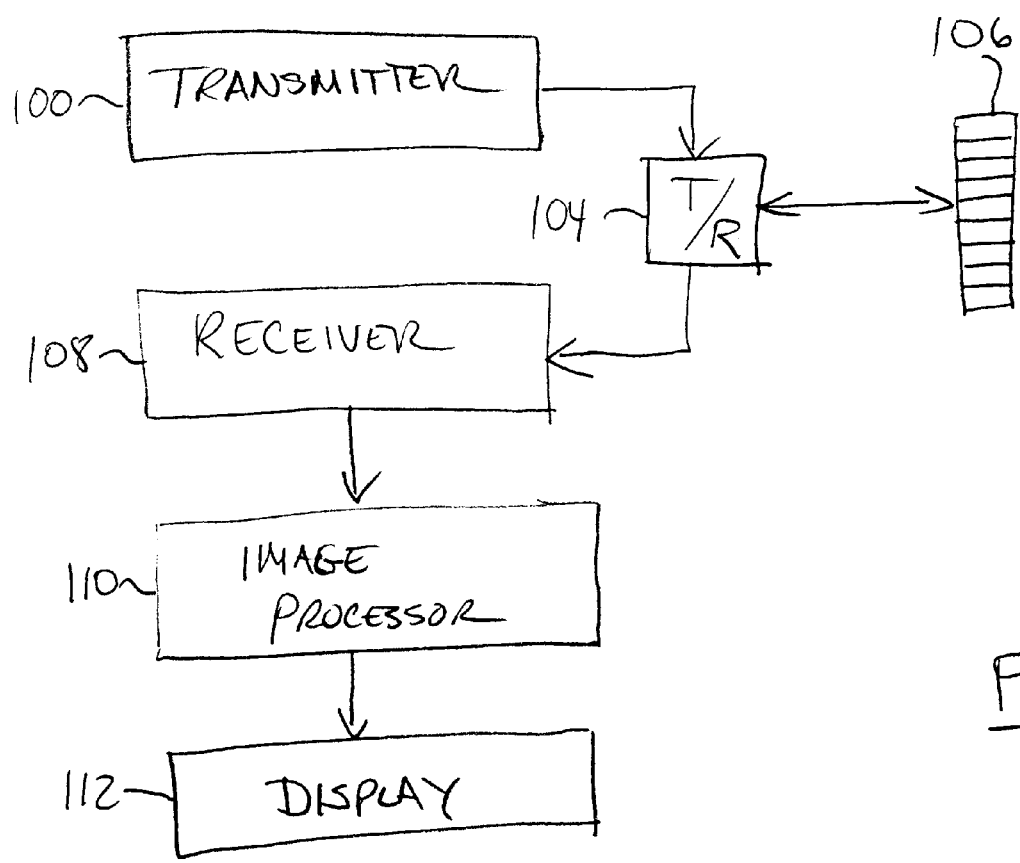
FIG. 14 is a block diagram of a medical diagnostic ultrasonic imaging system.

FIGS. 14–21 relate to a number of different embodiments for generating three-state transmit pulses, such as for example the three-state transmit pulse described above in conjunction with FIG. 8. These embodiments can also be used to generate other three-state transmit pulses, such as those described in Dodd, U.S. Pat. No. 5,833,614. As shown in FIG. 14, the transmitters described below can be used in a medical ultrasonic imaging system that includes a transmitter 100 and a receiver 108 that are coupled with a transducer array 106 by a transmit/receive switch 104. The transmitter 100 provides ultrasonic transmit waveforms or pulses to individual transducer elements included in the transducer array 106. These transmit waveforms are controlled in timing and phase to cause the transducer array 106 to create ultrasonic pulses that are directed into a body being imaged. Echoes from the body are converted by the transducer array 106 into receive signals that are applied to the receiver 108. The receiver 108 applies appropriate time delays and phase shifts to cause the receive signals to add coherently from selected regions within the body. The beam signals generated by the receiver 108 are applied via an image processor 110 to a display 112.

The elements 104 through 112 described above can take the widest variety of forms, and they are not limited to any specific embodiment. For example, the transducer array 106 can be a single-element array, or it can be an array in one or more dimensions. Any suitable technology can be used for the individual transducer elements of the array 106. The transmitter 100, receiver 108 and the image processor 110 can operate in any desired mode (e.g., B-mode, color Doppler mode, M-mode) at any desired frequency (e.g., fundamental, second harmonic or third harmonic), and contrast or therapeutic agents such as microbubbles may be used or not.

Figure 15:
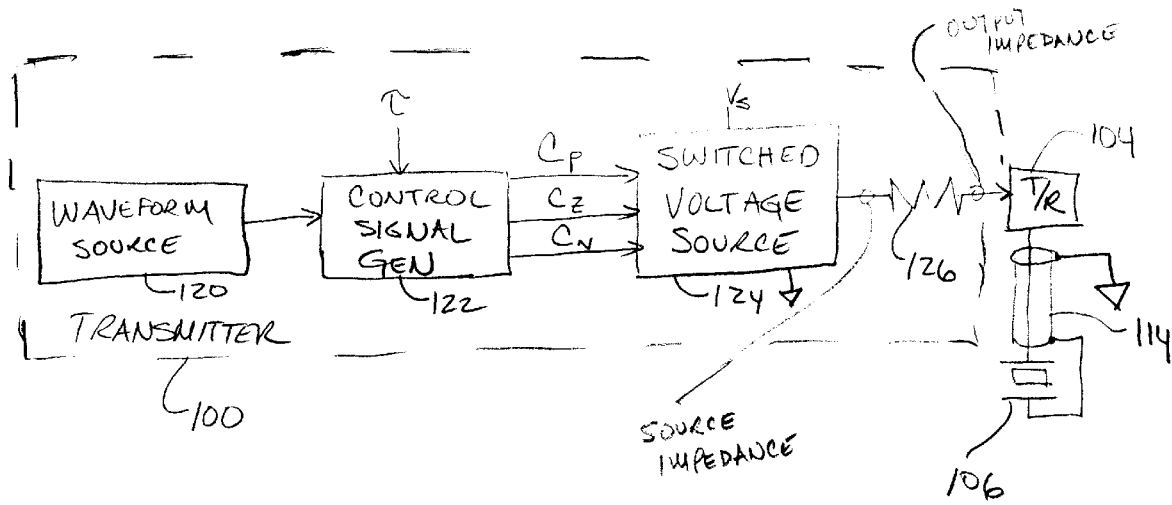
FIG. 15 is a block diagram of the transmitter and selected other components of the system of FIG. 14.

FIG. 15 shows a more detailed block diagram of one channel of the transmitter 100. As shown in FIG. 15, this channel is connected via the transmit/receive switch 104 and a shielded cable 114 to a respective transducer element 106.

The transmitter 100 includes for each channel a waveform source 120 that may for example be a digital memory storing an input waveform having desired frequency characteristics. The input waveform is applied as an input to a control signal generator 122, which generates three control signals $C_p$, $C_n$, and $C_z$. These control signals are applied to a switched voltage source 124 that generates a three-state output signal (+V, 0V, −V) at a low source impedance. This three-state waveform is applied to an impedance matching circuit 126 that may be a single resistor. The output of the resistor 126 is the output of the transmitter 100, and it is characterized by a transmitter output impedance. The impedance matching circuit 126 is optional, but it is provided in this case to match the transmitter output impedance with the characteristic impedance of the shielded cable 114. For example, the characteristic impedance of the cable 114 may be about 50 ohms, the resistance of the impedance matching circuit 126 may be about 40 ohms, and the source impedance may be about 10 ohms in each of the three output states of the switched voltage source 124.

Figure 16:
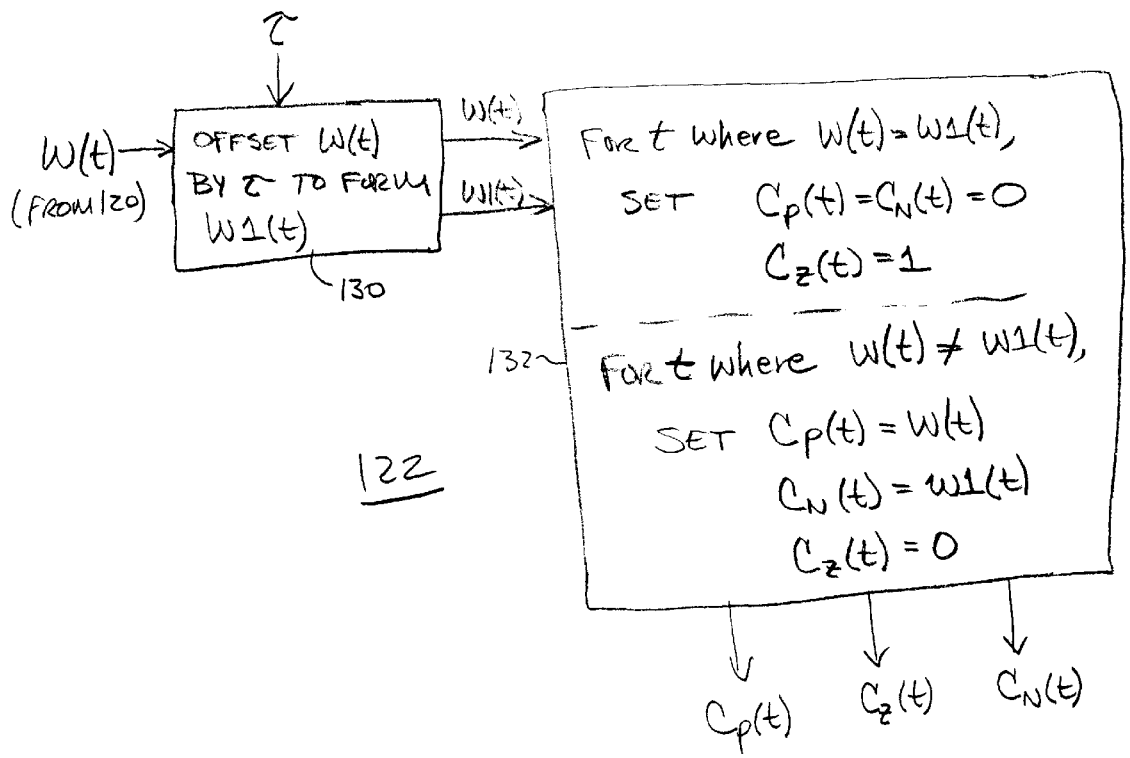
FIG. 16 is a block diagram of the control signal generator of FIG. 15.

FIG. 16 shows a block diagram of the control signal generator 122 of FIG. 15. The control signal generator 122 includes a stage 130 that accepts as an input the waveform W(t) and a signal c indicative of a desired time shift. The parameter $\tau$ may be positive or negative in alternative embodiments, and W(t) may for example be equal to W(t) discussed above in conjunction with FIG. 6. The stage 130 generates as an output the waveforms W(t) and W1(t). In this example W1(t) represents W(t) time shifted by $\tau$, without the inversion discussed above. As will be discussed below, positive values of W(t) are used to generate positive values of the output waveform at the +V level and positive values of the waveform W1(t) are used to generate negative values of the output waveform at the −V level. Thus, the inversion and summing discussed above are obtained via the operation of the switched voltage source, and there is no need to invert W1(t) in this embodiment to obtain the advantages discussed above.

In stage 132 the three control signals $C_p(t)$, $C_n(t)$, and $C_z(t)$ are generated as a function of the input signals W(t) and W1(t). In particular, for those values of t where W(t) is equal to W1(t), $C_p(t)$ and $C_n(t)$ are set equal to zero, and $C_z(t)$ is set equal to 1. For those values of t where W(t) is not equal to W1(t), $C_p(t)$ is set equal to W(t), $C_n(t)$ is set equal to W1(t), and $C_z(t)$ is set equal to zero.

Figure 17:
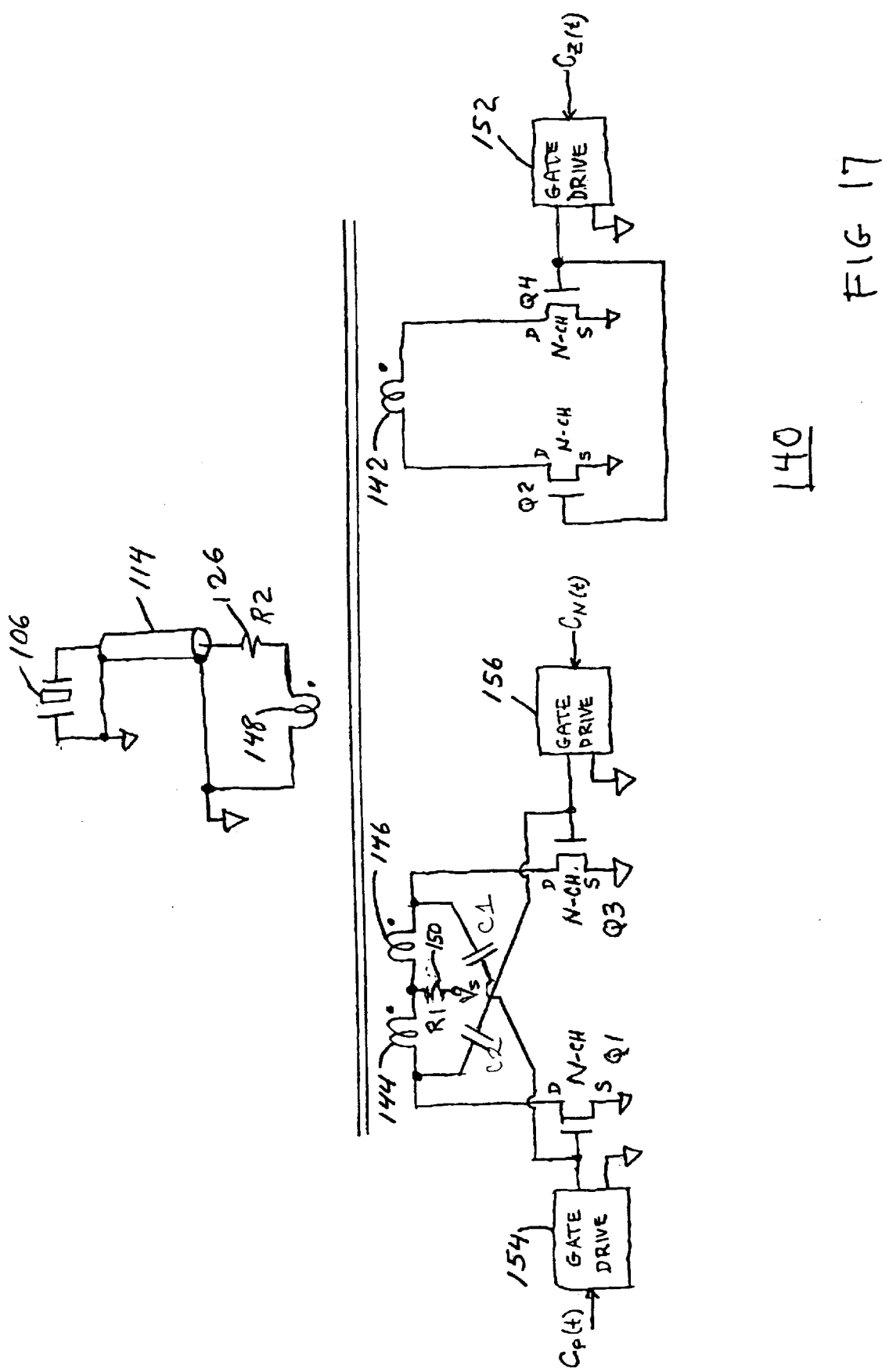
FIGS. 17, 18, and 19 are block diagrams of first, second, and third preferred embodiments of the switched voltage source of FIG. 15.

FIGS. 17–21 show various embodiments of the switched voltage source 124 of FIG. 15. For many applications, the embodiment 140 of FIG. 17 is preferred.

As shown in FIG. 17, the embodiment 140 includes a transformer having first, second and third primary windings 142, 144, 146, all inductively coupled to a secondary winding 148. Additionally, the winding 142 is DC isolated from all of the other windings 144, 146, 148. The secondary winding 148 is coupled via the impedance matching circuit 126 and the cable 114 with a transducer element 106. The first primary winding 142 is connected at each side to a reference voltage such as ground via a switching circuit that in this embodiment includes switches Q2, Q4. In this example the switches Q2, Q4 are implemented as FETs, though other switches can be used. The second and third primary windings 144, 146 are connected at a node that is in turn connected to a voltage source at $V_s$ via a resistor 150. The other sides of the second and third primary windings are connected to a reference voltage such as ground via switching circuits Q1, Q3, which in this embodiment also are implemented as FETs.

Each of the switching circuits Q1, Q2, Q3, Q4 switches between a high-resistance, open-circuit state and a low-resistance, closed-circuit state under the control of a respective gate driver 152, 154, 156. The gate driver 152 applies a control voltage to the gates of the switching circuits Q2, Q4 in parallel. The gate drivers 154, 156 apply control voltages to the gates of the switching circuits Q1, Q3, respectively. In this example the FETs used for the switching circuits Q1, Q2, Q3, Q4 are all N-channel devices having their sources connected to ground. For this reason, all of the gate drivers 152, 154, 156 can be referenced to ground as shown in FIG. 17. The gate drivers 152, 154, 156 are preferably implemented as conventional logic devices.

The gate driver 152 responds to the control signal $C_z(t)$ to place the switching circuits, Q2, Q4 in the closed-circuit state when $C_z(t)$ equals 1 and to place the switching circuits Q2, Q4 in the open-circuit state when $C_z(t)$ equals zero. The gate driver 154 places the switching circuit Q1 in the closed-circuit and open-circuit states when $C_p(t)$ equals 1 and 0, respectively. Similarly, the gate driver 156 places the switching circuit Q3 in the closed- circuit and open-circuit states when the control signal $C_n(t)$ equals 1 and 0, respectively. The second and third primary windings 144, 146 are physically arranged with respect to the secondary winding 148 such that a positive voltage +V is induced at the output of the secondary winding 148 when the switching circuit Q1 is in the closed-circuit state and a negative voltage −V is induced at the output of the secondary winding 148 when the switching circuit Q3 is in the closed-circuit state. A zero voltage is induced at the output of the secondary winding 148 when the switching circuits Q2 and Q4 are in the closed-circuit state. In this example, each of the four windings 142, 144, 146, 148 has an equal number of turns, but any desired relationship can be used between the number of turns of the four windings. For example, the ratio 1:1:1:2 can be used for the number of turns of the windings 142, 144, 146, 148, respectively.

The embodiment 140 also includes capacitors C1, C2, one connected between the winding 144 and the gate of Q3, the other connected between the winding 146 and the gate of Q1. These capacitors C1, C2 are optional, and the embodiment 140 functions well without them. However, they speed up the switching of the FETs Q1 and Q3, which is an advantage in some applications. For example, when the ultrasonic center frequency is 2 MHz, square wave components that are 1/32 of the period of the center frequency are only 15.6 nS in duration, and high speed switching is essential.

The capacitors C1, C2 perform a neutralization function, as described in *Radio Engineers' Handbook*, F. E. Terman, McGraw-Hill, First Edition, pp. 468, 469 (1943), to speed charging of a capacitance. The capacitance of each capacitor C1, C2 is selected to be approximately equal to the gate-to-drain capacitance (the "Miller capacitance") of one of the FETs Q1, Q2. Each capacitor C1, C2 feeds back to its respective gate driver a current of equal magnitude but of opposite phase of that required to charge the respective FETs Miller capacitance, thereby reducing FET switching time.

The neutralization currents supplied by the capacitors C1, C2 reduce the switching times for the respective switching circuits. Such neutralization currents may be used with a wide variety of switches in addition to the FETs described above, and such currents may be coupled capacitively, inductively, or resistively to the switching circuits. Neutralization currents may be generated in other ways than that illustrated, as for example by additional windings included in the transformer.

It is not essential in all embodiments that the switching circuit including Q2 and Q4 connect the first primary winding 142 to ground, or to any other reference voltage. As an alternative, this switching circuit can be implemented as any suitable device that selectively applies a low resistance across the first primary winding 142. Suitable modifications can be made to the gate driver 152 in this event.

By way of example only, the components of Table 1 have been used in the embodiment of FIG. 17.

TABLE 1

Preferred Components for FIG. 17 Embodiment

| Component | Identification |
| --- | --- |
| Q1, Q2, Q3, Q4 | Supertex TD9944 Dual N-channel enhancement-mode Vertical DMOS FET |
| R1 | 4.64 ohms resistor |
| R2 | 51.1 ohms resistor |
| Gate Driver 154, 156 | 74 ACT 244 CMOS logic buffer |
| C1, C2 | 6.8 pF 500 V monolithic ceramic capacitor |
| Transformer (including all four windings 142, 144, 146, 148) | 10 turns of #36 quadrafilar magnet wire wound on a Ferronics 12-350-J core |

The supply voltage $V_s$ is preferably set based on the imaging mode and the transducer. In pulse modes, $V_s$ would typically be set in the range +40VDC to +100VDC. In CW Doppler modes, $V_s$ would typically be set to a lower voltage, e.g., +3VDC to +1 0VDC.

The embodiment 140 of FIG. 17 is efficient, because the switching circuits Q1 and Q3 operate as switches, and thus have a low impedance (e.g. 5 ohms) when conducting current. Similarly, the switching circuit including Q2 and Q4 also operates as a switch having a low impedance in the closed state. Thus, the source impedance of the embodiment 140 (measured between the secondary winding 148 and the impedance matching circuit 126 looking toward the primary windings 142, 144, 146) is low in all three voltage states (+V, 0V, −V). As another important advantage, the source impedance of the embodiment 140 is substantially constant in all three voltage states. In the 0V state, this source impedance is equal to the resistance of two FETs when fully conducting. Each FET has a resistance of about 5 ohms by way of example, and thus the source impedance is about 10 ohms in the 0V state. In the +V state the source impedance is equal to the impedance of Q1 plus the impedance R1 of the resistor 150. Because in this example all four of the switching circuits Q1, Q2, Q3, Q4 are identical, the impedance of Q1 is equal to the impedance of Q2 or Q4. By setting the resistance R1 equal to the closed-circuit impedance of one of the FETs Q1, Q2, Q3, Q4, the source impedance in the positive voltage state +V is also equal to 10 ohms. Finally, in the negative voltage state the source impedance is equal to R1 plus the closed-circuit impedance of Q3, or 10 ohms in this example.

The largest of the three source impedances for the +V, 0V, and −V states is preferably no more than four times, more preferably no more than three times, and most preferably no more than two times the smallest of the three source impedances, measured at an ultrasonic frequency such as 2, 4 or 6 MHz. The three source impedances are preferably all less than 70 ohms, more preferably all less than 50 ohms, and most preferably all less than 20 ohms, measured at an ultrasonic frequency such as 2, 4 or 6 MHz. The largest of the three source impedances differs from the smallest of the three source impedances preferably by less than 70 ohms, more preferably by less than 50, 30 or 10 ohms, and most preferably by less than 5 ohms, measured at an ultrasonic frequency such as 2, 4 or 6 MHz. The transducer elements included in the array 106 have a characteristic impedance at an ultrasonic frequency such as 2, 4 or 6 MHz, and all three source impedances are preferably less than this characteristic impedance.

The resistor 150 also acts as a safety fuse in case either Q1 or Q3 should fail as short circuits. In the event of such a failure, the very high non-pulsing current through the resistor 150 will cause it to fail as an open circuit, thereby preventing further damage. In the event the resistor 150 fails as an open circuit, it effectively disconnects the respective channel from the power supply, and allows the remaining transmit channels to continue operation.

The output impedance of the transmitter 100 is the sum of R2 plus the source impedance seen looking back into the output winding of the transformer.

When Q2 and Q4 are in the closed-circuit state, they apply a very low impedance across the first primary winding 142. This low impedance is reflected to the secondary winding 148 and is equal to the source impedance. Since Q2 and Q4 are used only to drive the output to zero, they do not have to have any DC voltage applied to their drains. They can be switched on for as long or short a time as required, but they will not draw current from the power supply. Q2 and Q4 provide a low source impedance in the 0V state, but they waste no power in the +V and −V states. Q2 and Q4 provide the 0V, low source impedance state at the times required within the transmit waveform and also for the times that the transmitter is idle, such as when the respective transmitter channel is apodized off and during receive.

The embodiment 140 develops the electrical transmit signal that is applied to the transducer element at three separate voltage levels that define the waveform shape (e.g., the waveform of FIG. 8). For all three of these voltage levels, the source impedance of the switched voltage source is controlled to be a predetermined value. This switched voltage source is very efficient in converting input DC power into an output AC waveform.

The switched voltage source uses few components, takes up very little space, and is inexpensive to manufacture. It interfaces simply and directly to a digital waveform generator such as the control signal generator 122. The high efficiency of the switched voltage source means that a smaller power supply can be used to generate a given desired acoustic output power level, and that less heat is dissipated by the ultrasound system. These factors reduce the total complexity, cost, size and cooling requirements of the ultrasound system.

The switching circuit coupled to the first primary winding 142 actively drives the output voltage to 0V at low source impedance. In this way the inefficiencies associated with a shunt resistor coupling the transducer element to ground are avoided, and high speed, symmetrical switching is provided both from the +V level to the 0V level and from the −V level to the 0V level.

The switched voltage source allows high-speed slewing of the supply voltage $V_s$ without accidentally triggering a transmit pulse. In some applications it is desirable to slew the supply voltage between high and low values at high speed (e.g. 100V for a B-mode scan line and 5V for a CW Doppler scan line). Because the embodiment 140 uses ground-referenced sources of the FETs, gate drivers with low source impedance, and a symmetrical topology for the transformer windings and FETs, this circuit is highly immune to falsely emitting a transmit pulse when the supply voltage $V_s$ is slewed rapidly. If the changing supply voltage causes a transient current to flow through the windings 144, 146 to charge the output capacitance of the FETs Q1, Q3, the fields due to the two currents will cancel in the secondary winding 148. Any resultant current due to imperfect matching between the two FETs Q1 and Q3 and between the two transformer windings 144, 146 can develop only a very low voltage at the secondary winding 148 because of the low shunting impedance of the zero voltage state FETs Q2, Q4.

Because the supply voltage $V_s$ can be slewed rapidly in the embodiment 140, it is well suited in imaging methods in which multiple transmit power levels are used to image and selectively burst blood-borne microbubbles. For example, a first, lower transmit power level is used to image blood-borne microbubbles with little bursting of the microbubbles, and then the transmit power level is rapidly increased to a level that bursts microbubbles at a much higher rate. If desired, the transmit power level is then rapidly decreased to the first level for continued imaging at the original, low level of microbubble bursting. This imaging method may be performed at fundamental or harmonic frequencies, and the microbubbles may be either conventional microbubbles (filled with a gas such as perfluorocarbon) or therapeutic microbubbles (filled with a therapeutic agent such as a chemotherapy compound for cancer treatment). Conventional microbubbles are well suited for perfusion studies, where the microbubbles are destroyed with high-powered transmit pulses and then low-powered transmit pulses are used to measure the rate at which the imaged tissue is re-perfused. Therapeutic microbubbles are well suited to deliver therapeutic agents to selected tissues, by first imaging the selected tissue at low power to detect the arrival of therapeutic microbubbles in the bloodstream, and then transmitting high-powered transmit pulses focused to burst microbubbles in the selected tissue and thereby deliver the therapeutic agent contained in the microbubbles.

These imaging and therapeutic methods may be practiced with any of the embodiments described herein. Suitable transmit pulses may be used, including but not limited to the transmit pulses described elsewhere in this specification. In some applications, it may be preferable to use two-state transmit pulses, where the pulse is made up of positive and negative levels relative to a central voltage (e.g. 0VDC) that is applied to the transducer element before and after the pulse.

The switched voltage source is balanced and highly symmetrical, and this results in very low residual flux in the transformer at the end of a transmit pulse. For this reason, the transducer elements and receivers can operate effectively a short time after the end of the transmit pulse for extremely short-range imaging. Such shallow-depth imaging is an important advantage for some applications.

Important advantages of the embodiment 140 can be summarized as follows:

1. The embodiment 140 provides a symmetrical circuit that is well suited for avoiding distortion of the type that leads to undesired second harmonic frequency components.

2. All of the switching circuits are N-channel devices.

3. All of the switching circuits can be fabricated in a single integrated circuit.

4. All of the gate drivers generate positive voltages referenced to ground, and they are therefore easily and inexpensively implemented by logic gates.

5. All of the switching circuits are operated as switches and provide low resistance when in the closed-circuit state. This ensures high operating efficiency.

6. The source impedance is controlled to a low, uniform value in all three output states (+V, 0V, −V).

7. The 0V switching circuit Q2, Q4 drives the output to 0V at a low source impedance and thereby speeds the transition to the 0V state.

8. The embodiment is highly resistant to generating false transmit pulses when the supply voltage is slewed rapidly.

9. The transformer provides DC isolation for fault tolerance and increased patient safety.

10. The resistor 150 acts as a fuse that in the event of an FET short isolates a single transmitter channel while allowing other channels to function normally.

11. The embodiment is small in size, uses few components with few connections and is low in cost.

12. The control signals are digital signals that can be generated by logic gates.

13. The control signal for the 0V switching circuits Q2, Q4 can easily be derived as a simple logical NOR of the drive for the other FET switching circuits Q1, Q3.

14. The balanced, highly symmetrical design of the embodiment 140 reduces residual flux in the transformer at the end of a transmit pulse, and thereby enhances short-range imaging.

The low, constant source impedance in all three states makes it easier to model, analyze, predict and obtain controlled, repeatable performance of the combined transmitter, cable and transducer element.

Figure 18:
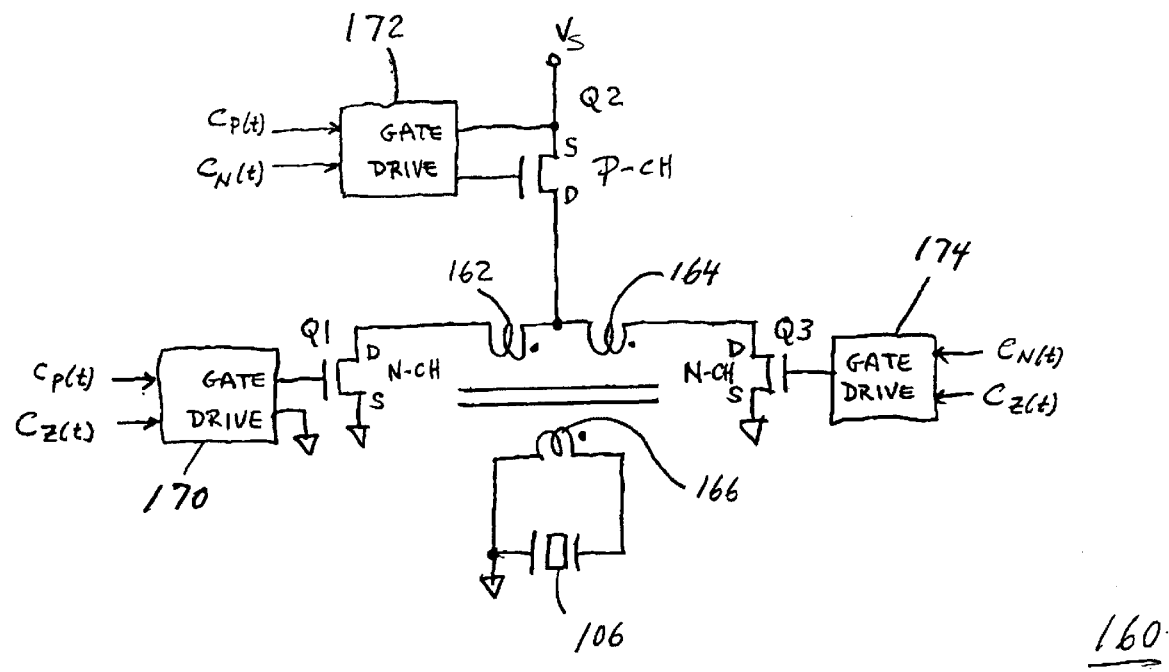

The 0V switching circuit Q2 and Q4 drives the output voltage to zero as Q1 or Q3 is turning off. Thus, as the resistance of Q1 or Q3 is going up the resistance of Q2 and Q4 is going down. For this reason, the voltage across the transducer element is actually driven toward 0 volts by both mechanisms. In a similar manner Q2 and Q4 maintain the voltage across the transducer element at approximately 0 volts as the rising voltage on the drain of Q1 or Q3 charges the respective output capacitance during turn off. FIG. 18 shows a block diagram of a second embodiment 160 of the switched voltage source 124 of FIG. 15. The embodiment 160 includes a transformer having two primary windings 162, 164 interconnected at a node that is connected via a switching circuit Q2 to a voltage source at $V_s$. The primary windings 162, 164 are inductively coupled to a secondary winding 166 that is connected to a transmitter element 106. In FIG. 18 the interconnection cable is not shown, and no impedance matching circuit is used. The primary windings 162, 164 are connected to ground via respective switching circuits Q1, Q3. The switching circuits Q1, Q2, Q3 are switched on and off by gate drivers 170, 172, 174, respectively. The gate drivers 170, 172, 174 respond to the control signals described above in conjunctions with the embodiment 140. In this case, the switches Q1, Q3 are both turned on when $C_z(t)$ is in a logic 1 state, the switching circuits Q1 and Q2 are both turned on when the control signal $C_p(t)$ is in the logic 1 state, and the switching circuits Q2 and Q3 are both turned on when the control signal $C_n(t)$ is in the logic 1 state. In the embodiment 160 the switching circuits Q1, Q2, Q3 are all operated as switches such that they have a low resistance when in the closed-circuit state. The switching circuits Q1 and Q3 can be implemented as N-channel FETs having their sources connected to ground, and the switching circuit Q2 can be implemented as a P-channel FET having its source connected to $V_s$.

The embodiment 160 provides many of the advantages discussed above in conjunction with the embodiment 140. The main exception is that the switching circuit Q2 is in this embodiment a P-channel FET, and the gate driver 172 is not referenced to ground.

Figure 19:
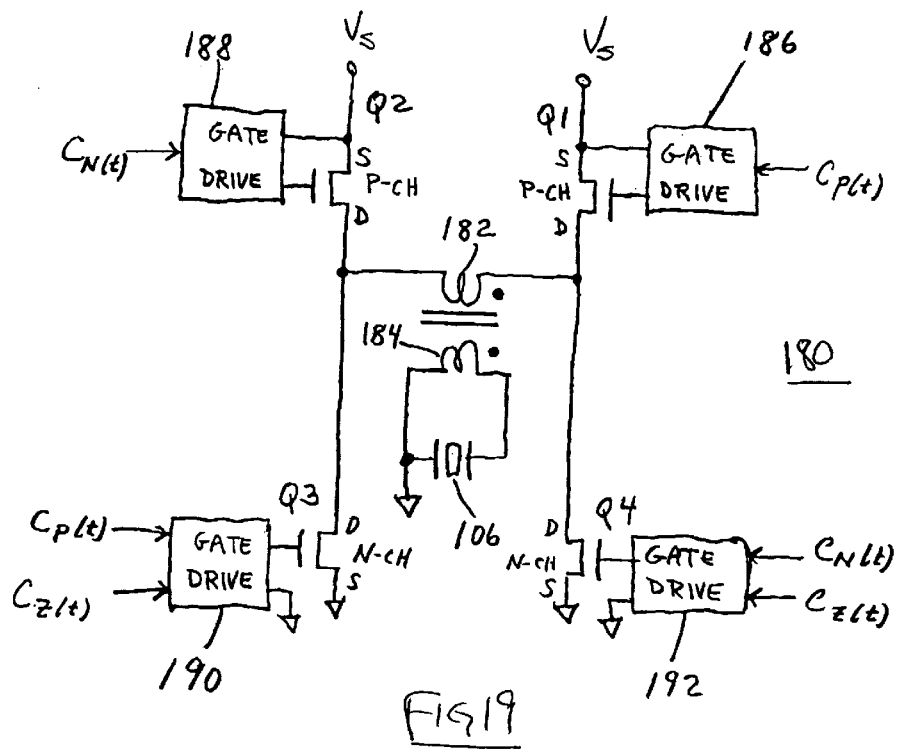

The embodiment 180 of FIG. 19 includes a transformer having a single primary winding 182 and a single secondary winding 184 that are inductively coupled. The transducer element 106 is connected across the secondary winding 184, and the primary winding 182 is connected across two nodes.

The left-hand node is connected to $V_s$ by a switching circuit Q2 and to ground by a switching circuit Q3. The right-hand node is connected to $V_s$ by a switching circuit Q1 and to ground by a switching circuit Q4. The switching circuits Q1, Q2, Q3, Q4 are switched between an open-circuit state and a closed-circuit state by respective gate drivers 186, 188, 190, 192. As before, the switching circuits Q1, Q2, Q3, Q4 operate as switches, and can be implemented as FETs. The switching circuits Q1 and Q2 can be implemented as P-channel FETs having their sources connected to $V_s$, and the switching circuits Q3, Q4 can be implemented as N-channel FETs having their sources connected to ground.

In the 0V state the gate drivers 190, 192 place the switching circuits Q3, Q4 in the closed-circuit state, thereby driving the transducer element 106 to 0V with low source impedance. In the positive voltage state the gate drivers 186, 190 turn on the switching circuits Q1, Q3 to apply a voltage of +V at low source impedance to the transducer element 106. In the negative voltage state the gate drivers 188, 192, turn on the switching circuits Q2, Q4 to place a −V voltage on the transducer element 106 at low source impedance. The primary difference between the embodiment 180 and the embodiment 140 described above is that two of the switching circuits Q1, Q2 are implemented as P-channel FETs, and two of the gate drivers 186, 188 are referenced to $V_s$ rather than to ground.

Figure 20:
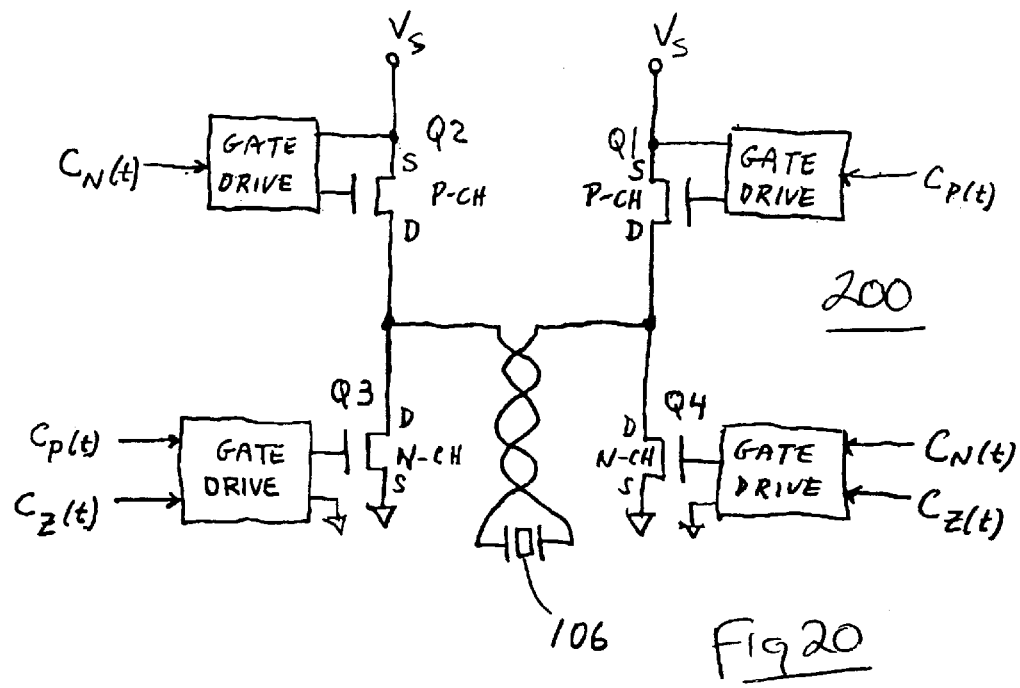
Figure 21:
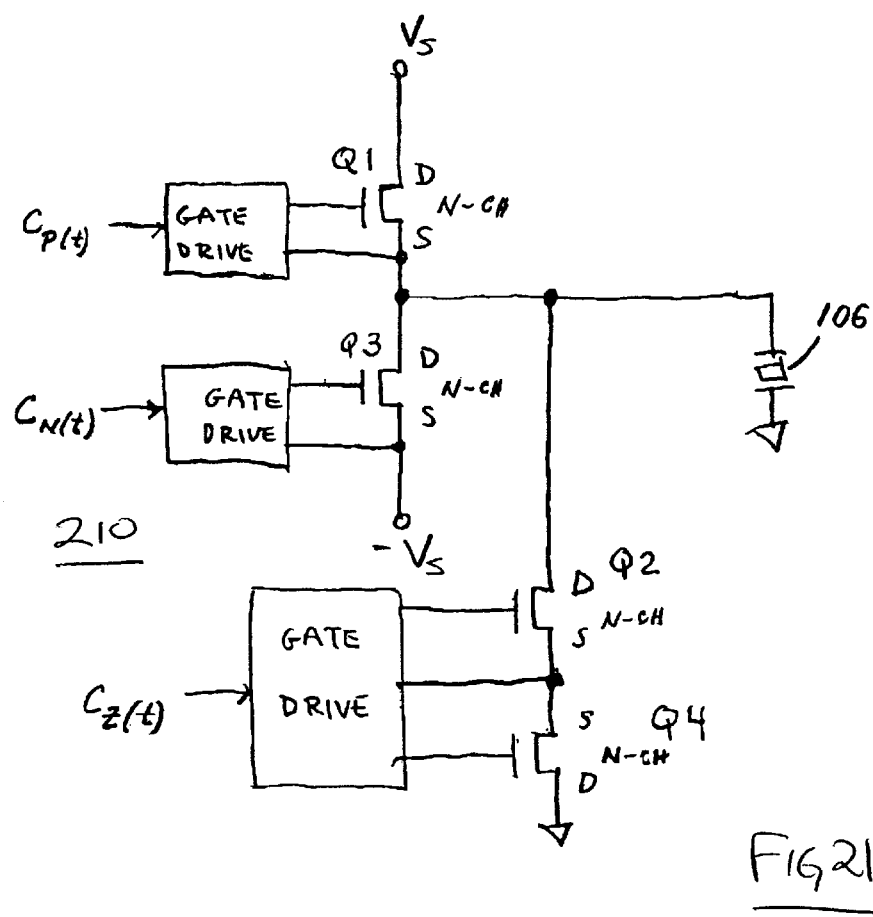

It is not essential in all embodiments that the switching circuits be coupled to the transducer element inductively with a transformer. In the embodiments of FIGS. 20 and 21 the switching circuits are conductively coupled to the transducer element 106. The embodiment 200 of FIG. 20 operates quite similarly to the embodiment 180 described above, except that the transformer windings 182, 184 are replaced with an interconnecting balanced cable such as a twisted pair.

The embodiment 210 of FIG. 21 uses a voltage source supplying voltages at $V_s$ and $-V_s$. A first switching circuit Q1 when closed applies the +V voltage to the transducer element 106, and another switching circuit Q3 when closed applies the −V voltage to the transducer element 106. The switching circuits Q2, Q4 when closed connect the transducer element 106 to ground. Two switching circuits Q2, Q4 are used in this embodiment because FETs are preferred, and each FET includes a parasitic diode between the drain and the source of the FET. For this reason, each FET can only block current (i.e. only act as an open switch) in a single direction. Two FETs are therefore used in series for the switching circuits Q2, Q4, arranged source to source or drain to drain.

Of course, many changes and modifications can be made to the preferred embodiments described above. The baseline voltage $V_B$ (which is equal to the central 0VDC switched level in the preferred embodiments described above) can vary from zero volts, as appropriate for the particular application. For example, the baseline voltage $V_B$ may be set equal to 1.4 VDC, the positive voltage to 1.4 VDC+V, and the negative voltage to 1.4VDC−V. As another example, the secondary winding 148 of FIG. 7 can be conductively coupled to a voltage source at a non-zero baseline voltage $V_B$ instead of to ground as shown in FIG. 17. Additionally, the positive and negative voltages may differ from the baseline voltage by equal amounts (as described above), or by non-equal a mounts.

Moreover, the present invention is not limited to use with transmitters having only three discrete voltage states. Additional circuitry can be added to provide 5, 7, 9 or 11 discrete voltage states, and an even number of discrete voltage states may be provided for some applications.

As another example, the switching circuits can be implemented by other types of switches than the FETs illustrated. N-Channel devices may be substituted for P-channel devices, and vice-versa, and various types of impedance matching circuits and cable may be used or no impedance matching circuit and/or no cable may be used, as desired. Also, a switching circuit may include multiple switches in parallel such as multiple FETs to increase current carrying capacity.

A switching circuit may also use some connection of devices such as a cascode circuit or other cascaded switches to speed up switching. FIG. 22 shows a variation of the embodiment of FIG. 17 that includes FETs Q5 and Q6 connected in a cascode circuit with the FETs Q1 and Q3. In practice, $V_G$ would be fixed at a voltage selected to provide desired operating conditions for the FETs Q1 and Q3. Such cascode circuits can be used on any desired ones of the switching circuits.

Also, a switching circuit may be controlled by optical rather than voltage signals, and gate drive signals may be coupled to switches via transformers. If desired, more than four windings may be used in the transformer, and center-tapped windings may be avoided.

As used herein the term "square wave" is intended to include three-state waves, whether pulse width modulated or not.

The term "time shift" is intended broadly to encompass both positive and negative time shifts.

The term "positive voltage" or "negative voltage" is in each case intended to encompass a range of voltages.

The term "voltage source" is intended to mean a source of one or more voltages.

The term "set" means one or more.

The term "coupled with" is intended broadly to encompass inductive, conductive, capacitive, direct and indirect coupling. Thus, two elements are said to be coupled with one another whether or not there are intervening elements.

The term "source impedance" is intended to refer to the impedance of a voltage source prior to any impedance matching circuit.

The term "switching" is intended to refer to a circuit that switches between a closed-circuit, low-resistance state and an open-circuit, high-resistance state.

The term "ultrasonic frequency" is intended to refer to frequencies greater than or equal to about 1 MHz.

The term "selected ultrasonic frequency" is intended to refer to a frequency at which a transmit waveform generator operates, as for example the fundamental frequency of an ultrasonic pulse generated by the transmit waveform generator. In general, all of the impedance relationships discussed above refer to impedances at such selected ultrasonic frequencies.

The foregoing detailed description has been intended by way of illustration, not limitation. It is only the following claims, including all equivalents, that are intended to define the scope of this invention.

What is claimed is:

1. A transmit waveform generator for a medical ultrasonic imaging system, said generator comprising:
    a primary transformer winding;
    a first switching circuit coupled to both sides of the primary winding and operative to provide a low resistance path across the primary winding when the first switching circuit is in a closed-circuit state;
    a secondary transformer winding inductively coupled with the primary transformer winding and adapted to be coupled with a transducer element;
    said first switching circuit operative when in the closed circuit state to drive the transducer element to a baseline voltage.

2. The invention of claim 1 wherein the first switching circuit comprises first and second switches, each switch coupled between a respective side of the primary winding and a reference potential.

3. The invention of claim 1 further comprising a second primary winding inductively coupled to the secondary winding, said second primary winding coupled on one side to a voltage source and on the other side to a reference voltage via a second switching circuit;
    said second switching circuit operative when in a closed-circuit state to drive the transducer element to a second voltage, said second voltage being positive relative to the baseline voltage.

4. The invention of claim 3 further comprising a third primary winding inductively coupled to the secondary winding, said third primary winding coupled on one side to a respective voltage source and on the other side to a respective reference voltage via a third switching circuit;
    said third switching circuit operative when in a closed-circuit state to drive the transducer element to a third voltage, said third voltage being negative relative to the baseline voltage.

5. The invention of claim 4 wherein the second and third primary windings are coupled to the same voltage source and the same reference voltage.

6. The invention of claim 1 wherein the primary winding comprises first and second windings interconnected at a node, and wherein the invention further comprises a second switching circuit interconnecting the node to a voltage source.

7. The invention of claim 1 wherein the primary winding is connected to first and second nodes on respective sides of the primary winding, wherein the first switching circuit comprises first and second switches, each interconnecting a respective node to a respective reference potential, and wherein the invention further comprises;
    a second switching circuit interconnecting the first node to a respective voltage source; and
    a third switching circuit interconnecting the second node to a respective voltage source.

8. A transmit waveform generator for a medical ultrasonic imaging system, said generator comprising:
    a set of input conductors adapted for connection to at least one voltage source;
    an output conductor adapted for driving a transducer element;
    a first switching circuit coupled with the output conductor and operative to drive the output conductor to a baseline voltage at a first source impedance;
    a second switching circuit coupled with one of the input conductors and the output conductor and operative to drive the output conductor to a second voltage at a second source impedance, said second voltage being positive relative to the baseline voltage;
    a third switching circuit coupled with one of the input conductors and the output conductor and operative to drive the output conductor to a third voltage at a third source impedance, said third voltage being negative relative to the baseline voltage;
    wherein the largest of the first, second, and third source impedances is no more than four times the smallest of the first, second, and third impedances at a selected ultrasonic frequency.

9. The invention of claim 8 wherein the first, second and third source impedances are all less than about 70 ohms at the selected ultrasonic frequency.

10. The invention of claim 8 wherein the output conductor comprises a secondary transformer winding; and wherein the first, second and third switching circuits are inductively coupled with the secondary winding by first, second and third primary transformer windings, respectively.

11. The invention of claim 10 wherein each of the windings comprises an equal number of turns.

12. The invention of claim 8 wherein the first, second and third switching circuits each comprise at least one respective N-channel switch.

13. The invention of claim 8 wherein the first, second and third switching circuits each comprise at least one respective switch, and wherein the switches are substantially identical.

14. The invention of claim 8 wherein each of the switching circuits comprises at least one respective switch and at least one respective switch driver, and wherein all of the switch drivers are connected to a common voltage level.

15. The invention of claim 14 wherein all of the switches are connected to the same common voltage level as are the switch drivers.

16. The invention of claim 8 wherein the largest of the first, second, and third source impedances is no more than three times the smallest of the first, second, and third source impedances at the selected ultrasonic frequency.

17. The invention of claim 8 wherein the largest of the first, second, and third source impedances is no more than two times the smallest of the first, second, and third source impedances at the selected ultrasonic frequency.

18. The invention of claim 8 wherein the first, second, and third source impedances are all less than 50 ohms at the selected ultrasonic frequency.

19. The invention of claim 8 wherein the first, second, and third source impedances are all less than 20 ohms at the selected ultrasonic frequency.

20. A transmit waveform generator for a medical ultrasonic imaging system, said generator comprising:

a set of input conductors adapted for connection to at least one voltage source;

an output conductor adapted for driving a transducer element;

a first switching circuit coupled with the output conductor and operative to drive the output conductor to a baseline voltage at a first source impedance;

a second switching circuit coupled with one of the input conductors and the output conductor and operative to drive the output conductor to a second voltage at a second source impedance, said second voltage being positive relative to the baseline voltage;

a third switching circuit coupled with one of the input conductors and the output conductor and operative to drive the output conductor to a third voltage at a third source impedance, said third voltage being negative relative to the baseline voltage;

wherein the largest of the first, second, and third source impedances differs from the smallest of the first, second, and third impedances by less than 70 ohms at a selected ultrasonic frequency.

21. The invention of claim 20 further comprising:

a transducer cable; and a resistive element connected in series between the output conductor and the cable and characterized by a resistive impedance, wherein the first, second, and third source impedances are all less than the resistive impedance at the selected ultrasonic frequency.

22. The invention of claim 20 further comprising:

a transducer cable having a characteristic impedance;

wherein the first, second and third source impedances are all less than the characteristic impedance at the selected ultrasonic frequency.

23. The invention of claim 20 wherein the largest of the first, second, and third source impedances differs from the smallest of the first, second, and third source impedances by less than 50 ohms at the selected ultrasonic frequency.

24. The invention of claim 20 wherein the largest of the first, second, and third source impedances differs from the smallest of the first, second, and third source impedances by less than 30 ohms at the selected ultrasonic frequency.

25. The invention of claim 20 wherein the largest of the first, second, and third source impedances differs from the smallest of the first, second, and third source impedances by less than 10 ohms at the selected ultrasonic frequency.

26. The invention of claim 20 wherein the largest of the first, second, and third source impedances differs from the smallest of the first, second, and third source impedances by less than 5 ohms at the selected ultrasonic frequency.

27. A transmit waveform generator for a medical ultrasonic imaging system, said generator comprising:

a set of input conductors adapted for connection to at least one voltage source;

an output conductor adapted for driving a transducer element;

a first switching circuit coupled with the output conductor and operative to drive the output conductor to a baseline voltage at a first source impedance;

a second switching circuit coupled with one of the input conductors and the output conductor and operative to drive the output conductor to a second voltage at a second source impedance, said second voltage being positive relative to the baseline voltage;

a third switching circuit coupled with one of the input conductors and the output conductor and operative to drive the output conductor to a third voltage at a third source impedance, said third voltage being negative relative to the baseline voltage; and a transducer cable coupled with the output conductor, wherein the transducer cable has a characteristic impedance;

wherein the first, second, and third source impedances are all less than the characteristic impedance at a selected ultrasonic frequency.

28. A transmit waveform generator for a medical ultrasonic imaging system, said generator comprising:

a set of input conductors adapted for connection to at least one voltage source;

an output conductor adapted for driving a transducer element;

a first switching circuit coupled with the output conductor and operative to drive the output conductor to a baseline voltage at a first source impedance;

a second switching circuit coupled with one of the input conductors and the output conductor and operative to drive the output conductor to a second voltage at a second source impedance, said second voltage being positive relative to the baseline voltage;

a third switching circuit coupled with one of the input conductors and the output conductor and operative to drive the output conductor to a third voltage at a third source impedance, said third voltage being negative relative to the baseline voltage; and a transducer element coupled with the output conductor, wherein the transducer element has a characteristic impedance at an ultrasonic frequency;

wherein the first, second, and third source impedances are all less than the characteristic impedance at a selected ultrasonic frequency.

29. A transmit waveform generator for a medical ultrasonic imaging system, said generator comprising:

a set of input conductors adapted for connection to at least one voltage source;

an output conductor adapted for driving a transducer element;

a first switching circuit coupled with the output conductor and operative to drive the output conductor to a baseline voltage;

a second switching circuit coupled with one of the input conductors and the output conductor and operative to drive the output conductor to a second voltage, said second voltage being positive relative to the baseline voltage;

a third switching circuit coupled with one of the input conductors and the output conductor and operative to drive the output conductor to a third voltage, said third voltage being negative relative to the baseline voltage;

wherein the first switching circuit is switchable between an open-circuit state and a closed-circuit state; wherein the first switching circuit is characterized by a first impedance at a selected ultrasonic frequency when switched to the closed-circuit state to drive the output conductor to the baseline voltage; and wherein the first impedance dominates the first source impedance at the selected ultrasonic frequency when the first switching circuit is in the closed-circuit state.

30. The invention of claim 1, 8, 20, 27, 28 or 29 wherein the second and third switching circuits comprise respective switches, each switch comprising a respective gate and a respective drain, and wherein the invention further comprises first and second capacitors, each capacitor coupled between the gate of a respective one of the switches and the drain of the other switch.

31. The invention of claim 1, 8, 20, 27, 28 or 29 further comprising means for applying neutralizing currents to the second and third switching circuits to reduce switching times.

32. A transmit pulse generating method for a medical ultrasound imaging system, said method comprising:

(a) driving an output conductor coupled with a transducer element to a baseline voltage at a first source impedance with a first switching circuit during a first portion of an ultrasonic pulse characterized by a center frequency $f_0$ and an associated center period $\tau_0$ for a time period no less than $N*\tau_0/128$, where $N \geq 1$;

(b) driving the output conductor to a second voltage at a second source impedance with a second switching circuit during a second portion of the ultrasonic pulse, said second voltage being positive relative to the baseline voltage; and (c) driving the output conductor to a third voltage at a third source impedance with a third switching circuit during a third portion of the ultrasonic pulse, said third voltage being negative relative to the baseline voltage;

wherein the largest of the first, second, and third source impedances is no more than four times the smallest of the first, second, and third source impedances at a selected ultrasonic frequency;

wherein at least one of (b) and (c) is performed before (a) and at least one of (b) and (c) is performed after (a).

33. The method of claim 32 wherein the second and third voltages are adapted for ultrasonic imaging at a first, lower level of bursting of blood-borne microbubbles, and wherein the method further comprises:

(d) increasing the second and third voltages in magnitude such that the second and third voltages are adapted to burst blood-borne microbubbles at a second, higher level of bursting; and then (e) repeating (a), (b) and (c) in an order selected such that at least one of (b) and (c) is repeated before (a) is repeated, and at least one of (b) and (c) is repeated after (a) is repeated.

34. The method of claim 32 wherein the second and third voltages are adapted to burst blood-borne microbubbles at a first, higher level of bursting, and wherein the method further comprises:

(d) decreasing the second and third voltages in magnitude such that the second and third voltages are adapted for ultrasonic imaging at a second, lower level of bursting of blood-borne microbubbles; and then (e) repeating (a), (b) and (c) in an order selected such that at least one of (b) and (c) is repeated before (a) is repeated, and at least one of (b) and (c) is repeated after (a) is repeated.

35. A transmit pulse generating method for a medical ultrasound imaging system, said method comprising:

(a) driving an output conductor coupled with a transducer to a baseline voltage at a first source impedance with a first switching circuit during at least one of a period prior to an ultrasonic pulse and a period subsequent to the ultrasonic pulse;

(b) driving the output conductor to a second voltage at a second source impedance with a second switching circuit during at least one portion of the pulse, said second voltage being positive relative to the baseline voltage;

(c) driving the output conductor to a third voltage at a third source impedance with a third switching circuit during at least one other portion of the pulse, said third voltage being negative relative to the baseline voltage;

wherein the largest of the first, second, and third source impedances is no more than four times the smallest of the first, second, and third source impedances at a selected ultrasonic frequency.

36. The method of claim 35 wherein the second and third voltages are adapted for ultrasonic imaging at a first, lower level of bursting of blood-borne microbubbles, and wherein the method further comprises:

(d) increasing the second and third voltages in magnitude such that the second and third voltages are adapted to burst blood-borne microbubbles at a second, higher level of bursting; and then (e) repeating (a), (b) and (c).

37. The method of claim 35 wherein the second and third voltages are adapted to burst blood-borne microbubbles at a first, higher level of bursting, and wherein the method further comprises:

(d) decreasing the second and third voltages in magnitude such that the second and third voltages are adapted for ultrasonic imaging at a second, lower level of bursting of blood-borne microbubbles; and then (e) repeating (a), (b) and (c).

38. The method of claim 33, 34, 35 or 36 further comprising:

(f) introducing microbubbles into a tissue to be imaged prior to (d).

39. The method of claim 33, 34, 35 or 36 wherein the microbubbles contain a therapeutic agent.

40. The method of claim 32, 33, 34, 35 or 36 wherein the ultrasonic pulse of (a), (b) and (c) is characterized by a fundamental frequency, and wherein the method further comprises:

forming an image based on harmonic echoes of the ultrasonic pulse.

41. A transmit pulse generator for a medical ultrasound imaging system, said generator comprising:

(a) switching circuit means for driving an output conductor coupled with a transducer element to a baseline voltage at a first source impedance during a first portion of an ultrasonic pulse characterized by a center frequency $f_0$ and an associated center period $\tau_0$ for a time period no less than $N*\tau_0/128$, where $N \geq 1$;

(b) switching circuit means for driving the output conductor to a second voltage at a second source impedance during a second portion of the ultrasonic pulse, said second voltage being positive relative to the baseline voltage; and (c) switching circuit means for driving the output conductor to a third voltage at a third source impedance during a third portion of the ultrasonic pulse, said third voltage being negative relative to the baseline voltage;

wherein the largest of the first, second, and third source impedances is no more than four times the smallest of the first, second, and third source impedances at a selected ultrasonic frequency.

42. The invention of claim 32 or 41 wherein the source impedances of (a), (b) and (c) are all substantially equal at the selected ultrasonic frequency.

43. The invention of claim 32 or 41 wherein $N \geq 2$.

44. The invention of claim 32 or 41 wherein $N \geq 4$.

45. The invention of claim 32 or 41 wherein $N \geq 8$.

46. The invention of claim 1, 8, 20, 27, 28, 29 or 41 wherein the transmit waveform generator drives the transducer element with only three discrete voltage levels.

47. The invention of claim 1, 8, 20, 27, 28, 29 or 41 wherein the transmit waveform generator drives the transducer element with no more than eleven discrete voltage levels.

48. The invention of claim 1, 8, 20, 27, 28, 29, 32 or 41 wherein the baseline voltage is substantially equal to 0VDC.

49. A method for applying voltages to a medical ultrasonic imaging system transducer, said method comprising:

(a) providing a two-state waveform W(t);

(b) offsetting W(t) by a selected time interval to form an offset waveform W1(t);

(c) switching a first voltage to the transducer in response to W(t) when W(t) is not equal to W1(t); and (d) switching a second voltage to the transducer in response to W1(t) when W(t) is not equal to W1(t).

50. The method of claim 49 wherein the first voltage is positive and the second voltage is negative relative to a baseline voltage.

51. The method of claim 49 further comprising:

(e) switching a third voltage intermediate the first and second voltages to the transducer when W(t) and W1(t) are equal.

52. The method of claim 49 further comprising:

(e) varying the selected time interval.

53. A method for applying voltages to a medical ultrasonic imaging system transducer, said method comprising:

(a) providing a two-state waveform W(t);

(b) offsetting W(t) by a selected time interval to form an offset waveform W1(t);

(c) during times when W(t) and W1(t) are equal, setting a first and second control signal to a first logic state and a third control signal to a second logic state;

(d) during times when W(t) and W1(t) are not equal, setting the first control signal in response to W(t), the second control signal in response to W1(t), and the third control signal to the first logic state;

(e) switching a first voltage to the transducer in response to the third control signal;

(f) switching a second voltage to the transducer in response to the first control signal, said second voltage being positive relative to the first voltage;

(g) switching a third voltage to the transducer in response to the second control signal, said third voltage being negative relative to the first voltage.

54. The method of claim 53 further comprising:

(a) varying the selected time interval.

55. A transmit pulse in a medical ultrasonic imaging system, said pulse comprising at least three voltage levels and comprising first and second components that add to form the pulse, said first component substantially corresponding to a square wave signal alternating between a baseline voltage $V_B$ and a second voltage $V_B+V$, said second component corresponding to an inverted version of the square wave signal alternating between the baseline voltage $V_B$ and a third voltage $V_B-V$, time shifted by a selected time interval.

56. A pulse transmitter in a medical ultrasonic imaging system, said transmitter comprising:

a transducer; and a transmit waveform generator operative to apply a transmit pulse to the transducer, said pulse comprising at least three voltage levels and comprising first and second components that add to form the pulse, said first component substantially corresponding to a square wave signal alternating between a baseline voltage $V_B$ and a second voltage $V_B+V$, said second component corresponding to an inverted version of the square wave signal alternating between the baseline voltage $V_B$ and a third voltage $V_B-V$, time shifted by a selected time interval.

57. The invention of claim 55 or 56 wherein the baseline voltage $V_B$ is substantially equal to 0VDC.

* * * * *